United States Patent [19]

Collen

[11] Patent Number: 4,623,718
[45] Date of Patent: Nov. 18, 1986

[54] NOVEL COMPOSITION OF MATTER OF ANTITHROMBIN III BOUND TO A HEPARIN FRAGMENT

[75] Inventor: Désiré J. Collen, Winksele, Belgium

[73] Assignee: KabiVitrum AB, Stockholm, Sweden

[21] Appl. No.: 503,105

[22] Filed: Jun. 10, 1983

[30] Foreign Application Priority Data

Jun. 10, 1982 [SE] Sweden .............................. 8203611

[51] Int. Cl.$^4$ .................... C07K 17/10; A61K 31/725; A61K 37/64; C08B 37/10
[52] U.S. Cl. ....................................... 530/393; 536/21
[58] Field of Search ................. 260/112 B; 514/56, 8, 514/21; 536/21

[56] References Cited

U.S. PATENT DOCUMENTS

| | | | |
|---|---|---|---|
| 4,213,962 | 7/1980 | Miura et al. | 514/56 X |
| 4,301,153 | 11/1981 | Rosenberg | 514/56 |
| 4,303,651 | 12/1981 | Lindahl et al. | 514/56 |
| 4,351,938 | 9/1982 | Barnett | 514/56 X |
| 4,386,025 | 5/1983 | Jordan | 260/112 B |
| 4,415,559 | 11/1983 | Suzuki et al. | 514/56 |
| 4,446,126 | 5/1984 | Jordan | 514/56 |
| 4,526,714 | 7/1985 | Feijen et al. | 260/112 R |
| 4,533,549 | 8/1985 | Lasker | 514/56 |

FOREIGN PATENT DOCUMENTS 0137356  4/1985  European Pat. Off. ............. 514/56
81/03276 11/1981  PCT Int'l Appl. .

OTHER PUBLICATIONS

Chem. Abstracts, vol. 96, 1982, 195744h, Ceustermans et al.
Chem. Abstracts, vol. 98, 1983, 213439k, Hoylaerts et al.
The Merck Index, "Warfarin", Ninth Ed., 1976, p. 1294.
J. Clin. Invest., 75, 1169–1173(1985), Mansson et al.
FEBS Letters, 143, No. 1, Jun. 1982, 96–100, Björk et al.
Merck Index, 10th ed., 1983.
Collen et al., Thrombosis Haemostasis, 46 185 (1981).
Jordan et al., The Journal of Biological Chemistry, vol. 254, No. 8, pp. 2902–2913 (1979).
Ceustermans et al., The Journal of Biological Chemistry, 257, No. 7, 3401–3408 (published Apr. 10, 1982).
Danielsson et al., Biochem. J. (1981) 193, 427–433 (note here on p. 427 the lower limit 6,000).

Primary Examiner—Howard E. Schain
Attorney, Agent, or Firm—Pollock, Vande Sande & Priddy

[57] ABSTRACT

Novel chemical compounds which are heparin fragments with a molecular weight of from 2,000 to 5,500 covalently bound to antithrombin III, and their use in medicine.

4 Claims, No Drawings

NOVEL COMPOSITION OF MATTER OF ANTITHROMBIN III BOUND TO A HEPARIN FRAGMENT

FIELD OF THE INVENTION

The present invention relates to new chemical compounds consisting of heparin fragments covalently bound to antithrombin III, methods for their preparation, pharmaceutical compositions containing them and their use in therapy.

BACKGROUND OF THE INVENTION

Heparin, a sulfate-containing polysaccharide, is widely used clinically as a parenterally administered agent for the treatment and prevention of thrombosis. However, a very significant problem at heparin therapy is that the half life of heparin in blood is short, or about 1.5 hours. Because of this, heparin must ordinarily be administered by continuous intravenous infusion or by subcutaneous injection two to three times per 24 hours.

Presence of the plasma protein antithrombin III is a necessary prerequisite for the anticoagulation activity of heparin. Antithrompin III inhibits most of the coagulation enzymes which are formed at the blood coagulation. But these inhibition reactions are slow and insufficient to prevent blood from coagulating. When heparin is present, it is bound to antithrombin III and activates said antithrombin III to form an inhibitor with a greatly increased reactivity which is sufficient to prevent the coagulation. The heparin-antithrombin bound in this inhibitor is not covalent bound but is reversible.

Collen et al, Abstracts VIII Int. Congr. Thromb. Haemostasis, Thrombos. Haemostas. 46, 185 (1981), describe a product obtained by covalent coupling of standard heparin to antithrombin III. The products obtained had the properties of rapidly inhibiting the coagulation enzymes thrombin and activated Factor X. The products were shown in tests on rabbits to have a half life in blood which was two to three times longer than the half life of standard heparin. However, even though this represents a step forward, there is a need for heparin products with longer half life in blood and accordingly with longer duration of therapeutic activity. The present invention provides such heparin products with a very long half life in blood and correspondingly long duration of anticoagulation activity.

DESCRIPTION OF THE INVENTION

It has been found according to the present invention that novel compounds consisting of heparin fragments with a molecular weight less than 5,500, covalently bound to antithrombin III, have a half life in blood which is up to 30 times longer than the half life of standard heparin and about 10 times longer than the antithrombin III-standard herparin product described by Collen et al in the prior art. The novel compounds of the present invention rapidly inactivate activated coagulation Factor X, which indicates a high anticoagulant activity.

The heparin fragments contained in the novel compounds of the invention have a molecular weight of 5,500 or less, suitably from 2,000 to 5,500. Such fragments are prepared in known manner, for example by nitrous acid degradation of standard heparin, as is described for example in European patent publications No. 0 014 184 and No. 0 048 231.

The novel compounds of the present invention may be prepared in a three step process as follows.

In a first step, amino groups are introduced into the heparin fragments. This can be done by reacting carboxylic groups which are present in the heparin fragments with a suitable amine such as hexamethylenediamine. This reaction is carried out in the presence of a suitable coupling agent such as a carbodiimide, for example 1-ethyl-3-(3-dimethylaminopropyl)-carbodiimide. Care must be taken so that not all of the carboxylic groups react. The resulting modified heparin fragments will contain on average between 1 and 2 $NH_2$ groups per fragment.

Alternatively, amino groups can be introduced into the heparin fragment by limited N-desulfation or by converting the heparin fragments so that they will contain aldehyde functions.

In a second step, the amino groups introduced on the heparin fragments are reacted with a bifunctional reagent which is suitable to give substituted heparin fragments capable of reacting with the amino groups in antithrombin III. A suitable such bifunctional reagent is tolylene-2,4-diisothiocyanate. This reagent is suitably used in excess. The use of tolylene-2,4-diisothiocyanate will give a reactive isothiocyanate substituted heparin fragment.

In the third step the reactive substituted heparin fragment obtained in the second step is reacted with antithrombin III. In this reaction, the amino groups contained in the antithrombin III molecule will react with the isothiocyanate groups in the isothiocyanate substituted fragments and yield a reaction product which is a stable, identifiable, and novel chemical compound. In this third step, the heparin fragments will bind to antithrombin III with a 1:1 stoichiometry.

It will be understood that the skilled worker will be able to vary and choose the particular reagents used in the above reaction sequence without departing from the scope of the invention. For example, among coupling agents to be used in the first reaction step may be mentioned bromcyan activation of heparin before addition of diamine. Coupling of heparin fragment directly to antithrombin III through formation of Schiff base between the terminal aldehyde group of the heparin fragment and amino groups in antithrombin III can also be visualized.

In clinical practice, the novel compounds of the inventions will be used generally in the same manner and in the same form of pharmaceutical preparations as commercially available heparin for clinical use. Thus, the novel heparin derivatives of the present invention may be incorporated in aqueous solution for injection or in ointment preparations for administration via the skin and mucuous membranes.

The intermediate products obtained consisting of heparin fragments containing amino groups are also novel. They represent an additional aspect of the invention. Also the aldehyde form of the heparin fragments are novel compounds and represent an aspect of the invention. In the said aldehyde form, one terminal group in the heparin fragments contains an aldehyde function.

The invention will be further illustrated by the following working examples.

Preparation of Heparin Fragments Used as Starting Material by Depolymerization of Standard Heparin with Nitrous Acid

EXAMPLE 1

Heparin (0.5 g), isolated from the intestines of swine and dissolved in 150 ml water, was cooled to +4° C. and passed through a 3×7 cm column, Dowex®50 W–X8 (H+-form), 200–400 mesh. The column was thereafter washed with 100 ml water, whereafter the washing liquid was combined with the eluate containing purified heparin. To the combined fluid was added 250 ml dimetoxietan (glyme), cooled to −20° C., and 10 ml isoamylnitrit, and the mixture, which had a temperature of about +10° C., was allowed to stand for two minutes. Thereafter the reaction was interrupted by adding 10 ml 10% Na+-acetate. After addition of 5.2 liter ethanol, precipitated carbohydrate (heparin derivative) was collected by centrifugation. The product was dissolved in 500 ml 0.05M NaCl-0.05M Tris-HCl, pH 7.4. This solution was fractionated in 100 ml portions by affinity chromatography on a column containing 75 ml antithrombin-agarose-Sepharose® (Pharmacia Fine Chemicals, Uppsala), about 5 mg protein per ml gel. The column was eluted with a salt gradient (500 ml 0.05M NaCl-0.05M Tris-HCl in the mixing vessle; 500 ml 3M NaCl-0.05M Tris-HCl in the reservoar, whereby the major part of the applied material either passes, unretarded through the column or is eluted at low ion strength (0.4M NaCl); this material lacks biological activity. The active components (purified heparin derivatives) are eluted in a broad fraction between 0.5M NaCl and 3M NaCl corresponding to about 4% of the starting material. These fractions were pooled, concentrated and desalted by gel chromatography. Heparin derivatives, prepared and purified in this manner, had a molecular weight of between 3,000–5,000.

EXAMPLE 2

Covalent Coupling of Heparin Fragments to Antithrombin III

Step I

Amino groups were introduced into heparin fragments obtained as described above by dissolving 15 mg heparin fragments, prepared as described above in 4.5 ml water, followed by addition of 1 ml hexametylendiamine solution (21 mg/ml) and 2 ml of a solution of 1-ethyl-3-(3-dimethylaminopropyl)-carbodiimide hydrochloride (7.3 mg/ml). The pH of the solution was adjusted to 4.75 and the reaction mixture was allowed to stand during stirring for 20 minutes while pH was kept constant by addition of 0.1M HCl. The reaction was stopped by increasing pH to 9.5 using 2M NaOH. The reaction mixture was diluted to 3 times the original volume using 0.1M NaHCO3 buffer, pH 9.5, and was then dialyzed against 0.05M phosphate buffer pH 7.5 containing 0.05M NaCl.

Step II

The material obtained in Step I was separated in a low affinity fraction and a high affinity fraction by affinity chromatography on matrix bound antithrombin III in the same way as described in Example 1. Thereafter was added to 2.2 mg of the high affinity fraction 4 ml N,N-dimethyl-N-allylamine buffer pH 9.2 and 100 mg tolylene-2,4-diisothiocyanate. Thereafter nitrogen gas was bubbled through the solution for 1 minute, and the solution was incubated for one hour at 45° C. Thereafter 2 ml water was added and the suspension was extracted 4 times with 4 ml benzene and 3 times with heptane/ethylacetate (2/1) in order to remove excessive reagent.

Step III

The water phase obtained in Step II was thereafter immediately added to 20 ml 0.1M NaHCO3 buffer, pH 8.6, containing 50 mg antithrombin III. The mixture obtained was incubated for one hour at 30° C. under stirring and was then dialyzed against 0.02M imidazol-HCl buffer, 7.35 over night. The products formed were then purified by having the dialyzed reaction mixture pass a column, of DEAE-Sephadex, which then was eluted with a salt gradient 0–0.5M NaCl. The heparin fragment-antithrombin compound obtained were separated from unreacted antithrombin by affinity chromatography on heparin-Ultrogel column, equilibrated with 0.1M Tris-HCl buffer pH 7.6. The elution was made by a salt gradient (0.1–1.0M NaCl). The purified product obtained was homogenous in polyacrylamidelectrophores in the presence of sodium dodecyl sulphate. The molecular weight of the product obtained was from 65,000–80,000, with an average about 70,000, obtained in comparison with the molecular weight of proteins with known molecular weight. The product obtained inhibited activated Factor X with a second order rate constant of $0.92 \times 10^6 M^{-1} S^{-1}$. The yield with respect to heparin fragment-antithrombin III-compound was 24%.

Biological Half Life for the Compounds of the Invention

Two mg of the heparin fragment-antithrombin III compound obtained as described in Example 2, and where the heparin fragment was labelled with 3H, was dissolved in 1 ml 0.1M NaCl solution and injected into a vein in the ear of a rabbit. Thereafter a series of blood samples were taken during the next ten hours and radioactivity and inhibition of activated Factor X were measured. In this way, the biological half life for the tested compound was obtained. This half life was then compared with the half life for standard heparin, administered in the same manner.

The result of the test was that the half life of the heparin fragment-antithrombin compound according to the invention was 7.8 hours. This value was obtained using radioactivity measurements as well as biological activity measurements, that is Factor $X_a$-inhibition. The half life for standard heparin measured in the same way is 0.3 hours. Thus, the half life for the heparin fragment-antithrombin III compound was 26 times longer than the half life for standard heparin.

The great increase in biological half life which was obtained for the novel compounds of the present invention is very valuable clinically. In the present treatment with heparin, it is normal that two or three injections must be given per day at prophylactic treatment of post-operative thrombosis. Using the novel compounds of the present invention, it would be sufficient with one injection every two or every three days. This is a great improvement from the point of view of the patient and also from the point of view of the clinic because of the practical and economical advantages which follow from better utilized care resources.

Studies on antithrombotic effects of the heparin-fragment-antithrombin III Compound of the invention on the Wessler rabbit stasis model show that intravenous injection of the compound effectively prevents thrombus formation in the rabbits.

I claim:

1. A heparin fragment with a molecular weight of 2,000 to, 5,500 covalently bound to antithrombin III.

2. The heparin fragment bound to antithrombin III of claim 1 wherein the ratio of the heparin fragments to antithrombin III is 1:1.

3. The heparin fragment bound to antithrombin III of claim 1 wherein the heparin fragment, prior to being covalently bound to the antithrombin III, contains from 1 to 2 amino groups per fragment.

4. The heparin fragment bound to antithrombin III of claim 1 wherein the heparin fragment, prior to being covalently bound to the antithrombin III, includes one terminal group which contains an aldehyde function.

* * * * *